(12) United States Patent
Pommier

(10) Patent No.: US 10,188,531 B2
(45) Date of Patent: Jan. 29, 2019

(54) PROSTHESIS SOCKET WITH A RIGID STRUCTURE ARRANGED BETWEEN AN INTERNAL DEFORMABLE LAYER AND AN EXTERNAL DEFORMABLE LAYER

(71) Applicant: POMMIER ORTHOPEDIE, Villebon sur Yvette (FR)

(72) Inventor: Pascal Pommier, Massy (FR)

(73) Assignee: POMMIER ORTHOPEDIE, Villebon sur Yvette (FR)

( * ) Notice: Subject to any disclaimer, the term of this patent is extended or adjusted under 35 U.S.C. 154(b) by 0 days.

(21) Appl. No.: 14/502,896

(22) Filed: Sep. 30, 2014

(65) Prior Publication Data

US 2015/0094824 A1  Apr. 2, 2015

(30) Foreign Application Priority Data

Oct. 1, 2013 (FR) ..................................... 13 59511

(51) Int. Cl.
*A61F 2/80* (2006.01)
*B29C 47/00* (2006.01)
(Continued)

(52) U.S. Cl.
CPC .............. *A61F 2/80* (2013.01); *A61F 2/5046* (2013.01); *B29C 47/0004* (2013.01); *B29C 47/0066* (2013.01); *B29C 70/44* (2013.01); *A61F 2002/5053* (2013.01); *A61F 2002/5055* (2013.01); *A61F 2002/5056* (2013.01); *A61F 2002/805* (2013.01); *B29C 2793/009* (2013.01);
(Continued)

(58) Field of Classification Search
CPC ............. A61F 2/78; A61F 2/7812; A61F 2/80
See application file for complete search history.

(56) References Cited

U.S. PATENT DOCUMENTS 1,316,347 A * 9/1919 Bidou ....................... A61F 2/60
623/33
4,128,903 A    12/1978 Marsh et al.
(Continued)

FOREIGN PATENT DOCUMENTS

FR    2 539 616    7/1984
FR    2 828 093    2/2003

OTHER PUBLICATIONS

Machine Translation for FR 2828093 A1; Feb. 7, 2003.*

*Primary Examiner* — Marcia Watkins
(74) *Attorney, Agent, or Firm* — Pillsbury Winthrop Shaw Pittman LLP

(57) ABSTRACT

A socket to interface a lower limb which has undergone amputation and a modular element, includes a proximal portion allowing the lower limb that has undergone amputation to be inserted; a distal portion allowing the modular element to be fastened; an internal deformable layer made of silicone rubber, designed to be in contact with the lower limb that has undergone amputation; an external deformable layer made of silicone rubber; a structure made of rigid material arranged between the internal layer and the external layer, comprising at least two posts, each post extending substantially axially from a base on the distal side towards an end on the proximal side, the ends of the various posts being not linked, so as to separate from or approach each other due to the effect of deformation of the internal layer and of the external layer.

8 Claims, 5 Drawing Sheets

(51) Int. Cl.
*B29C 70/44* (2006.01)
*A61F 2/50* (2006.01)
*B29K 83/00* (2006.01)
*B29K 307/04* (2006.01)

(52) U.S. Cl.
CPC .... *B29K 2083/005* (2013.01); *B29K 2307/04* (2013.01)

(56) References Cited

U.S. PATENT DOCUMENTS

| | | | | |
|---|---|---|---|---|
| 5,387,245 A | * | 2/1995 | Fay | A61F 2/7843 623/34 |
| 5,724,714 A | * | 3/1998 | Love | A61F 2/7843 264/221 |
| 5,980,803 A | | 11/1999 | Slemker et al. | |
| 6,136,039 A | * | 10/2000 | Kristinsson | A61F 2/7812 623/36 |
| 6,231,617 B1 | * | 5/2001 | Fay | A61F 2/7812 623/36 |
| 8,591,599 B1 | * | 11/2013 | Kaliki | A61B 5/6828 600/372 |
| 2007/0027556 A1 | * | 2/2007 | Wilson | A61F 2/7812 623/36 |
| 2007/0276510 A1 | | 11/2007 | Becker et al. | |
| 2012/0179272 A1 | | 7/2012 | Dignam et al. | |
| 2013/0123940 A1 | * | 5/2013 | Hurley | A61F 2/80 623/33 |

* cited by examiner

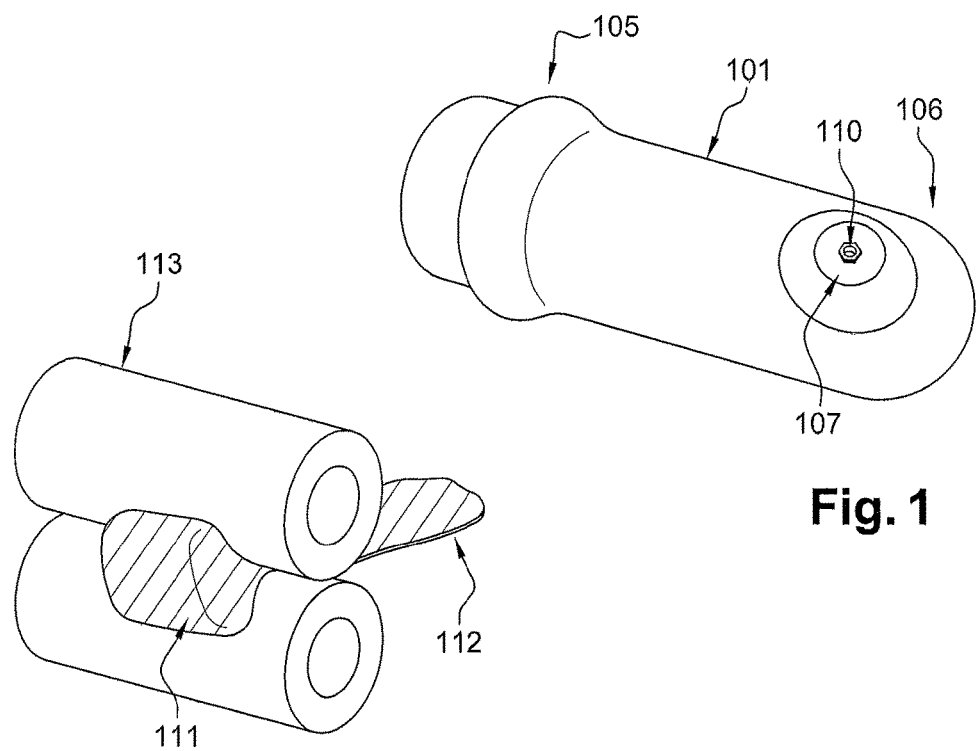
Fig. 1
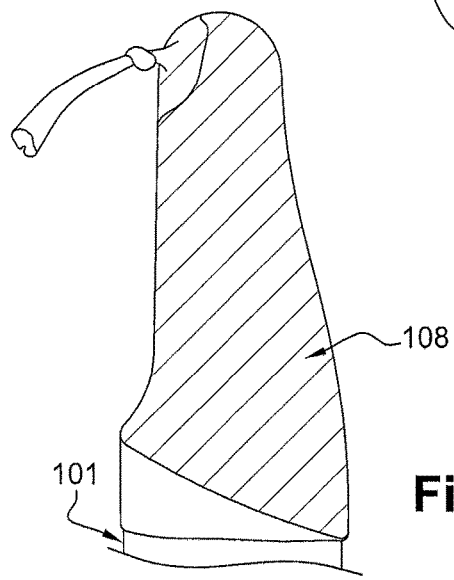
Fig. 2
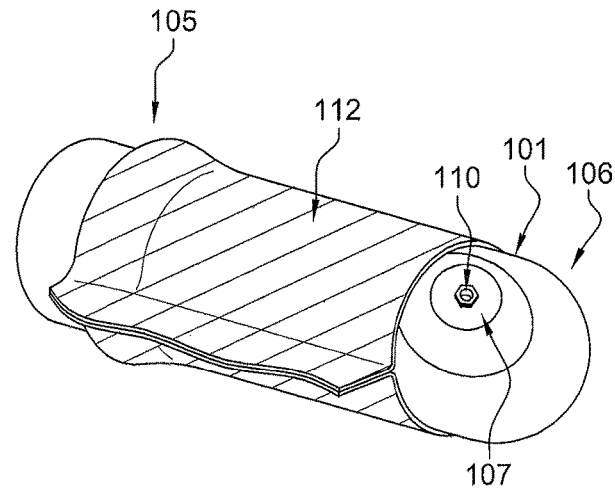
Fig. 3
Fig. 4

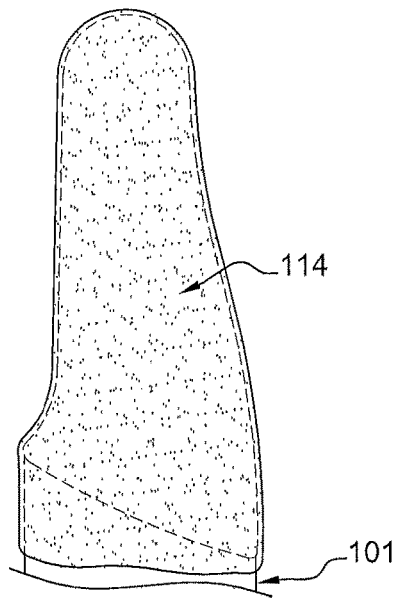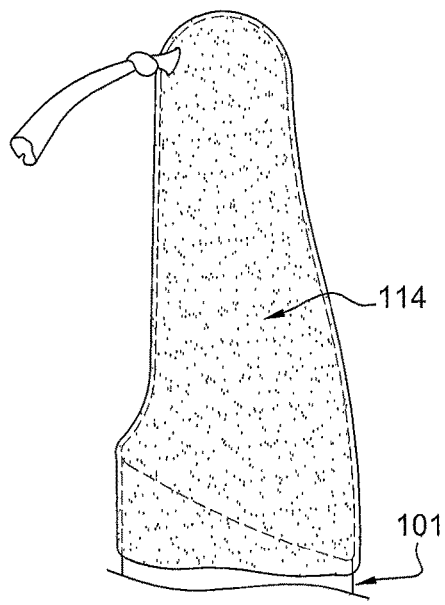
Fig. 5    Fig. 6
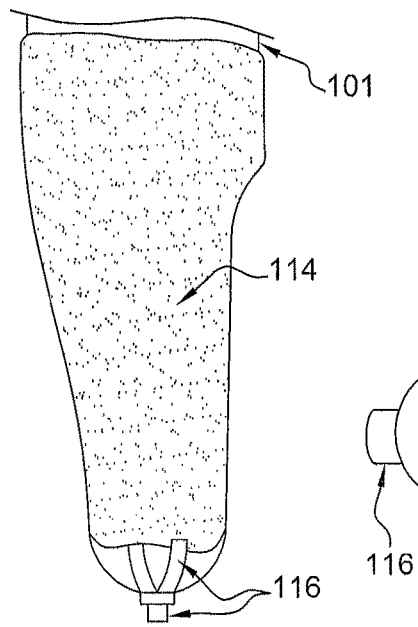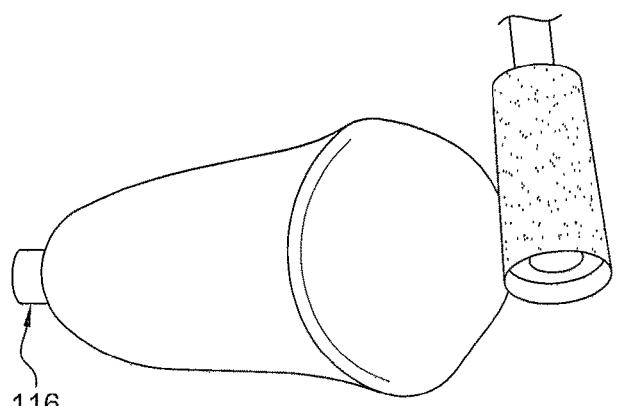
Fig. 7    Fig. 8

PROSTHESIS SOCKET WITH A RIGID STRUCTURE ARRANGED BETWEEN AN INTERNAL DEFORMABLE LAYER AND AN EXTERNAL DEFORMABLE LAYER

CROSS-REFERENCE TO RELATED APPLICATIONS

This application claims priority to French Patent Application No. 1359511, filed Oct. 1 2013, the entire content of which is incorporated herein by reference in its entirety.

FIELD

The invention relates to the medical field, and in particular to the field of prosthetic systems intended to replace a limb or joint which has undergone amputation. The invention relates more particularly to a prosthetic system socket used to interface a limb which has undergone amputation, also known as a stump, of the lower part of the body (leg) with a modular prosthesis element.

BACKGROUND

A prosthetic system for a lower limb conventionally comprises a prosthesis made up of modular elements (such as a knee, a tube and a foot) and a socket. The purpose of the socket is to receive a lower limb which has undergone amputation, and is used to suspend a modular element. The socket is made to measure so that it fits the shape and size of the lower limb that has undergone amputation.

Currently sockets are made of rigid or semi-rigid resin or plastic and comprise an external carbon structure. The socket must be comfortable, easy to put on and must fit well onto the lower limb that has undergone amputation, in particular in order for it not to loosen during the oscillation phase of walking.

Some sockets are placed directly in contact with the lower limb which has undergone amputation—these sockets are called "contact" sockets—but in order to resolve the aforementioned problem, it is known to call upon the use of an adaptor. The adaptor is intended to be placed inside the socket, and is most often made of silicone. Silicone is in effect a flexible material that can undergo deformation and which is comfortable. The adaptor facilitates fitting of the lower limb that has undergone amputation within the socket. It also serves a comfort function, with the adaptor providing contact with and absorbing shock on the lower limb that has undergone amputation within the socket, reducing any pain and improving the stump's tolerance.

These current sockets, however, exhibit several drawbacks:

The variations in the size of the lower limb that has undergone amputation are not taken into consideration, in particular when the lower limb which has undergone amputation is prone to swelling: the lower limb which has undergone amputation is then compressed within the socket. Such variations in volume may be due to muscular development, to a gain or loss in weight, or a vascular problem. The socket then no longer fits the lower limb that has undergone amputation and causes discomfort for the patient.

The need to fit an adaptor is a daily constraint on the patient, because of the possible complexity of the adaptor. A socket insert may also be used, which highly stresses the upper limbs.

The socket is uncomfortable in a sitting position due to its rigidity, as the socket does not adapt to the deformation of the lower limb that has undergone deformation.

The socket is uncomfortable when it is used for long periods.

The materials used in the design of contact sockets and the wear on the adaptors means that these devices must be renewed regularly.

The difficult of maintaining contact sockets in a proper hygienic condition is a recurrent problem observed amongst amputees.

The rotations of the socket in relation to the lower limb are difficult to control, in particular with systems of distal hook adaptors covered with fabric.

SUMMARY

An aspect of the invention proposes a socket which allows the aforementioned drawbacks to be resolved.

An embodiment of the invention therefore essentially relates to a socket for interfacing a lower limb which has undergone amputation with a modular element, comprising:
  a proximal portion allowing the lower limb that has undergone amputation to be inserted;
  a distal portion allowing the modular element to be fastened,
  an internal deformable layer made of silicone rubber, designed to be in contact with the lower limb that has undergone amputation;
  an external deformable layer made of silicone rubber;
  a structure made of rigid material arranged between the internal layer and the external layer, comprising at least two posts, each post extending substantially axially from a base located on the distal side towards an end located on the proximal side, where the ends of the posts are not linked, so as to separate from or approach each other due to the effect of deformation of the internal layer and of the external layer.

A post is an element of elongated form, comprising a base and an end, and which extends substantially axially from the base towards the end. The base is located on the distal side of the socket and the end is located on the proximal side of the socket. The bases of the various posts are firmly attached to one another. On the other hand, the ends of the various posts are not connected and are thus able to move apart from each other. It considered therefore that the posts can move apart from or towards each by separating or bringing together their ends. Naturally the posts are sufficiently wide and strong for the socket to support the body of the patient.

Since the silicone rubber is a material that is deformable, flexible and elastic, it provides the socket with elasticity, allowing it to adapt to variations in volume of the lower limb that has undergone amputation, as well as to variations in its shape (in the sitting position, for example). The use of an adaptor is therefore no longer necessary. When combined with the rigid posts structure, the silicone rubber gives the socket a dynamic character. Furthermore, the silicone rubber is strong, which is desirable, given that the socket according to an embodiment of the invention supports the weight of the patient's body: the inner layer and the external layer must not tear when the posts separate from each other.

Furthermore, at the internal layer the silicone rubber provides the patient with a degree of comfort. At the external layer, the silicone rubber gives an aesthetically pleasing appearance to the socket by covering the structure made of rigid material. The external layer made of silicone rubber also provides a solid connection and creates a dynamic effect between the various layers, which will thus act synergistically. It will be noted that the silicone rubber can contain pigment so as to give it the colour of the patient's skin. Moreover, the silicone rubber may be used in all available Shore hardness values, according to needs. It will also be noted that the silicone rubber absorbs few bodily substances, retains little odour and is easy to maintain.

Furthermore, the rigid material allows the socket to be held. The posts of the structure made of rigid material are beneficially spread substantially uniformly over the periphery of the socket. The posts are designed to move apart or closer together in accordance with variations in the volume of the lower limb that has undergone amputation, and depending on the movement performed or on the patient's position. A spring effect is achieved, with the silicone rubber acting as a shock absorber.

Besides the characteristics which have just been stated in the preceding paragraph, the socket according to an embodiment of the invention may exhibit one or more additional characteristics from amongst the following, considered individually or according to technically possible combinations:

In one non-restrictive embodiment, the rigid material comprises carbon. The carbon is in effect a strong and light material, and provides the socket with rigidity. A material made of glass fibre, polyamides, Kevlar (aramid), of lower strength, could be used to complement the carbon fibre.

In one non-restrictive embodiment, the rigid material structure comprises four posts. A first post is then intended to be positioned on the front face of the lower limb that has undergone amputation; a second post is intended to be positioned on the rear face of the lower limb that has undergone amputation. The last two posts are intended to be positioned on each lateral part of the lower limb that has undergone amputation. Thus when the patient is in a sitting position, the front and rear posts move towards each other, whereas the lateral posts move apart: the patient's comfort is optimised. Furthermore, this deformation prevents air entering at the proximal portion of the socket.

In a non-restrictive embodiment, at its distal portion the socket comprises a device for fixing (referred broadly as an attachment device) the modular element firmly to the structure made of rigid material. The fixing is thus solidly hooked to the socket and allows the weight of the prosthesis and of the patient to be supported.

An embodiment of the invention also relates to a method for making a socket for interfacing a lower limb that has undergone amputation with a modular element, comprising:
  making a positive which represents the lower limb that has undergone amputation, comprising a proximal zone and a distal zone;
  applying silicone rubber to the positive, so as to cover it with a layer known as the "internal layer";
  curing the positive covered with the internal layer;
  applying a layer of material that can be made rigid onto the positive covered with the internal layer so as to cover the latter;
  rigidifying the layer of material that can be made rigid;
  cutting the rigidified layer so as to form a rigid structure comprising at least two posts, each post extending substantially axially from a base located at the distal side towards an end located on the proximal side, where the ends of the posts are not connected.
  applying silicone rubber to the positive covered with the internal layer and with the rigid structure, so as to cover it with a layer known as the "external layer";
  curing the positive covered with the internal layer, the rigid structure and the external layer;
  de-moulding the assembly comprising the internal layer, the rigid structure, and the external layer from the positive.

The method described allows the socket described above to be made. It should be noted that all the steps of application of material are performed in an air-conditioned room in order to prevent the material hardening. The curing steps then allow the material to harden.

Besides the characteristics which have just been stated in the preceding paragraph, the method according to an embodiment of the invention may exhibit one or more additional characteristics from amongst the following, considered individually or according to technically possible combinations.

In one non-restrictive embodiment, the step for the application of silicone rubber onto the positive comprises the following sub-steps:
  extruding the silicone rubber so as to form at least one strip with a substantially constant thickness;
  covering at least one zone of the positive with the strip;
  filling out the distal portion of the positive;
  cutting and/or smoothing any residual excess thickness.

The strips are beneficially made using an electric carding machine. By the end of the step for application of the silicone rubber onto the positive, the positive is covered. Beneficially, several strips of the same thickness or even of different thicknesses are used, and placed on the positive, depending on the zones and according to needs.

In a non-restrictive embodiment, the method includes the following step between the rigidification step and the cutting step: withdrawing the rigidified layer from the positive covered with the internal layer. The rigid material may then be cut using an electric saw.

In a non-restrictive embodiment, the method comprises the following steps following the cutting step:
  positioning the rigid structure on the positive covered with the internal layer;
  bonding the rigid structure onto the internal layer.

In a non-restrictive embodiment, the method comprises the following steps, following the step for application of the internal layer on the positive:
  covering the positive covered with the internal layer with a soluble bag;
  creating a vacuum on the positive covered with the internal layer and the soluble bag.

In a non-restrictive embodiment, the method comprises the following steps, following the step for application of the external layer on the positive:
  creating a vacuum on the positive covered with the internal layer, the rigid structure and the external layer.

In a non-restrictive embodiment, the method comprises the following step:
  hooking a fastening device or fastener to the structure made of rigid material, designed to fit the modular element.

The invention and its various applications will be better understood on reading the following description and on examination of the figures which accompany it.

BRIEF DESCRIPTION OF THE FIGURES

The figures are only given for indication purposes and are in no way intended to limit the invention: The figures show:

In FIG. 1, a schematic representation of a step for fitting a jig for a de-pressurisation valve on a distal portion of a positive representing a lower limb which has undergone amputation, the step being carried out during a method for manufacturing a socket according to a non-restrictive embodiment of the invention;

In FIG. 2, a schematic representation of a silicone rubber extrusion step;

In FIG. 3, a schematic representation of a step for application of the extruded silicone rubber onto the positive;

In FIG. 4, a schematic representation of a step for creating a vacuum on the positive covered with silicone rubber;

In FIG. 5, a schematic representation of a step for application of carbon on the positive covered with silicone rubber;

In FIG. 6, a schematic representation of a step for creating a vacuum on the positive covered with silicone rubber and carbon;

In FIG. 7, a schematic representation of step for hooking a fastening device or fastener for the modular element, onto the carbon layer;

In FIG. 8, a schematic representation of a step for rubbing down the layer of carbon;

DETAILED DESCRIPTION

Unless otherwise stated, a given element appearing in different figures has the same unique reference number.

As aspect of the invention relates to a method for making a socket as well as to the socket obtained by the method. The manufactured socket is made to measure from a positive which represents a patient's lower limb that has undergone amputation. A fixing device, firmly attached to the socket, allows a modular element of a prosthesis to be fixed onto it, the prosthesis being made up of at least one modular element.

In order to minimise the risks of variation in the volume of the lower limb that has undergone amputation after wearing the socket that has been manufactured, several socket prototypes (made of plastic material) are trialled by the patient for one or more weeks, before' the method according to an embodiment of the invention used to manufacture the final socket is implemented. In effect, after the prosthetic system has been worn, the lower limb that has undergone amputation may develop muscle and thus change in size. It is desirable therefore to start with a positive which represents the lower limb that has undergone amputation after one or more weeks of use of the prosthesis.

Figure 13:
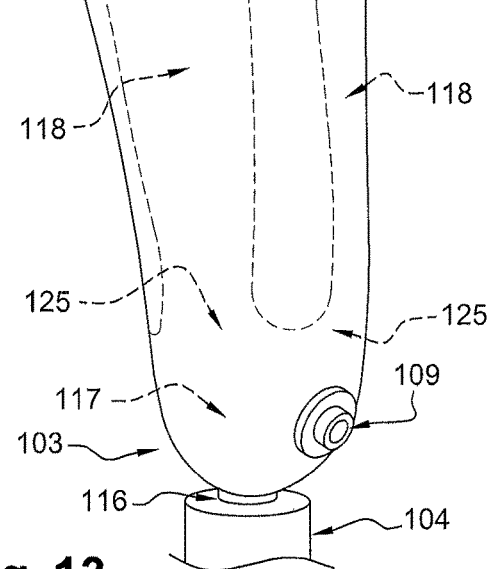
FIG. 13 shows a schematic representation of a socket according to a non-restrictive embodiment of the invention.
Figure 14:
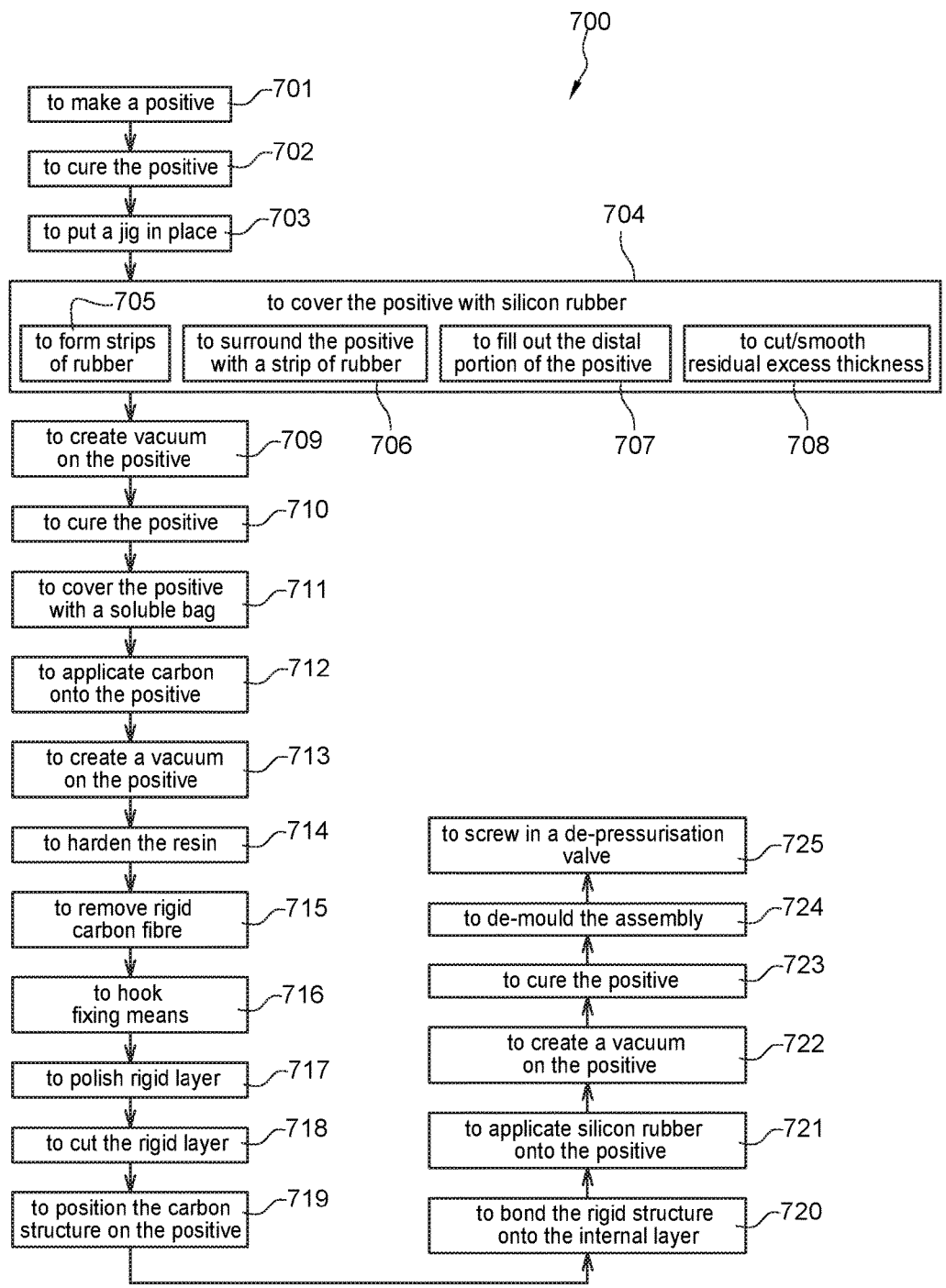
In FIG. 14, a diagram representing the steps of the method according to an embodiment of the invention.

In a non-restrictive embodiment, the method 700 for making a socket 100 (shown in FIG. 13) comprises the following steps, with reference to FIG. 14:

According to a step 701: making a positive 101, which can be seen in FIG. 1, which represents the lower limb that has undergone amputation. The socket is made by placing successive layers of material on the positive 101, which are then made rigid and then de-moulded from the positive 101. The socket 100 obtained comprises a proximal portion 102 and a distal portion 103. The closed distal portion 103 allows a modular element 104 to be fitted. The open proximal portion 102 allows the lower limb that has undergone amputation to be inserted. By analogy, it can be said that the positive also comprises a proximal zone 105 and a distal zone 106: the distal zone 106 represents the amputated end; the proximal zone 105 is the other end. The positive 101 is made from a negative made using plaster bandages or a digital device on the patient's lower limb that has undergone amputation. The positive 101 is beneficially made of plaster.

According to a step 702: curing the positive 101. In effect the plaster positive 101 is completely dry in order not to compromise the application of an internal layer of silicone rubber 108 (represented in FIG. 4) as described earlier. The positive made of plaster 101 is cured in a special oven until drying is complete.

According to a step 703: with reference to FIG. 1, putting in place 703 a jig 107 which comprises a fixing screw 110, onto the distal portion 106 of the positive 101. The jig can subsequently be used to fit a depressurisation valve 109 (shown in FIG. 13) using a nut/screw system. The circumference of the jib 107 has a hardness value which is greater than the hardness of the internal layer of the silicone rubber 108 described below, in order to enhance the strength of the valve 109 so as to ensure that the device operates correctly. In a subsequent step in the method, the valve 109 will sit in the location of the jig 107.

According to a step 704: application of a layer of silicone rubber 108 onto the positive 101, so as to cover it with a layer known as the "internal layer 108". It should be noted that this step is carried out in an air-conditioned area, whose ambient temperature is lower than the setting temperature of the silicone rubber. In effect, it is desirable that the silicone rubber remains pliable up until the desired moment. This step 704 comprises the following sub-steps:

According to a sub-step 705: with reference to FIG. 2, extruding at least one block of rubber 111 so as to form strips 112 of substantially constant thickness, where the thickness of the strips 112 may differ from one another. The extruded silicone rubber is beneficially a poly additive silicone rubber with a multiple choice of hardnesses expressed in terms of Shore hardness (with Shore 10 being its minimum hardness and Shore 90 being its maximum hardness). In a non-restrictive embodiment, two equal portions of the two-component silicone rubber are mixed in an electric carding machine 113 in order to create a synergistic body.

According to a sub-step 706: with reference to FIG. 3, surrounding the positive 101 with a strip 112 of silicone rubber. The strip 112 is worked with various tools so that it is a perfect fit on the positive 101, so that the latter has a regular surface. Beneficially, several strips 112 of different thicknesses are used and are placed in different zones of the positive 101, according to needs.

According to one sub-step 707: filling out of the distal portion of the positive 101 using a strip 112 made of silicone rubber. It should be noted that only the perimeter of the jig 107 is covered, so as to allow the valve 109 to be subsequently put in place, whilst ensuring that the device is leak-tight.

According to a sub-step 708: cutting and/or smoothing any residual excess thickness.

At the end of the step 704 for application of the silicone rubber on the positive 101, the positive 101 is covered.

According to a step 709: with reference to FIG. 4, creating vacuum on the positive 101 covered with the internal layer 108. The creation of the vacuum ensures that the silicon rubber 108 makes good contact on the positive 101, by removing any residual air between the positive 101 and the internal layer of the silicone rubber 108.

According to a step 710: curing the positive 101 covered with the internal layer 108 in order to harden the silicone rubber.

According to a step 711: covering the positive 101 covered with the internal layer 108 with a soluble bag, of the PVA type. This allows the internal layer 108 of the carbon resin 118 which will be over-laminated to be isolated, in order that the carbon 114 can subsequently be easily separated from the silicone rubber 108. It should be noted that the soluble bag can be moistened to make it more flexible.

According to a step 712: with reference to FIG. 5, application onto the positive 101 covered with the internal layer 108, of a laminated or pre-impregnated carbon 114, so that the positive is covered. The carbon 114 is impregnated with resin. It will be noted that a pre-impregnated carbon fibre is lighter than laminated carbon fibre but needs more time for application.

According to a step 713: with reference to FIG. 6, creating a vacuum on the positive 101 covered with the internal layer 108 and with carbon fibre 114. In effect, in order to carry out the lamination or the pre-impregnation, the carbon fibre and resin are placed under vacuum in order to ensure good impregnation of the fabric, in order to create a composite material which is free of imperfections.

According to a step 714: hardening of the resin so as to form a layer of rigid carbon 114. Hardening is achieved by catalytic reaction for conventional lamination, and by thermosetting for the pre-impregnated carbon.

According to a step 715: removing the layer of rigid carbon fibre 114 from the positive 101 covered with the internal layer 108. The soluble bag facilitates de-moulding of the layer of rigid carbon fibre 114.

According to a step 716: with reference to FIG. 7, hooking a fixing device (or fastener) 166 of the modular element 104 to the rigid layer 114. The fixing device or fastener 116 (anchorage) is bonded to the rigid layer 114 and then firmly attached to the latter using a second resin and carbon lamination covering a portion of the fixing device 116. The alignments of the socket 100 and of the modular element 104, which are pre-defined during the trialling, are preserved using an alignment transfer table.

According to a step 717: with reference to FIG. 8, rubbing down and polishing of the rigid layer 114.

Figure 9:
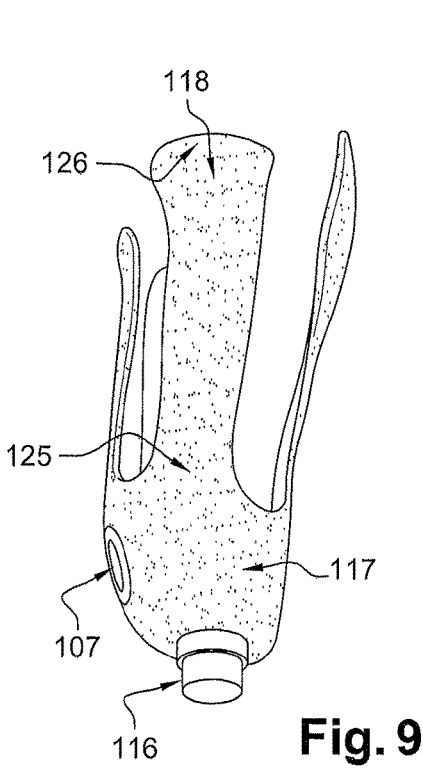
In FIG. 9, a schematic representation of a step for cutting the layer of carbon to form a rigid structure comprising posts.

According to a step 718: with reference to FIG. 9, cutting the rigid layer 114, so as to form a carbon fibre structure 117 comprising at least two posts 118, each of the posts 118 extending from a base located on the distal portion side 103, towards an end 126 located on the proximal portion side 102. The number of posts 118, their location and their dimensions depend on the amputation, the patient's needs and the dynamic effects desired by the prosthesis specialist. The configuration and the sensitivity of the lower limb that has undergone amputation, the morphology and the sex of the patient also influence these variables.

Figure 10:
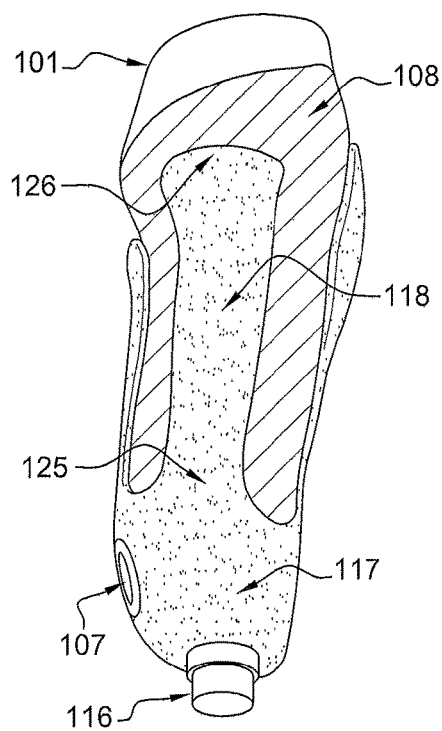
In FIG. 10, a schematic representation of a step for positioning of the rigid structure on the positive covered with silicone rubber.

According to a step 719: with reference to FIG. 10, positioning the carbon structure 117 on the positive 101 covered with the internal layer 108.

Figure 11:
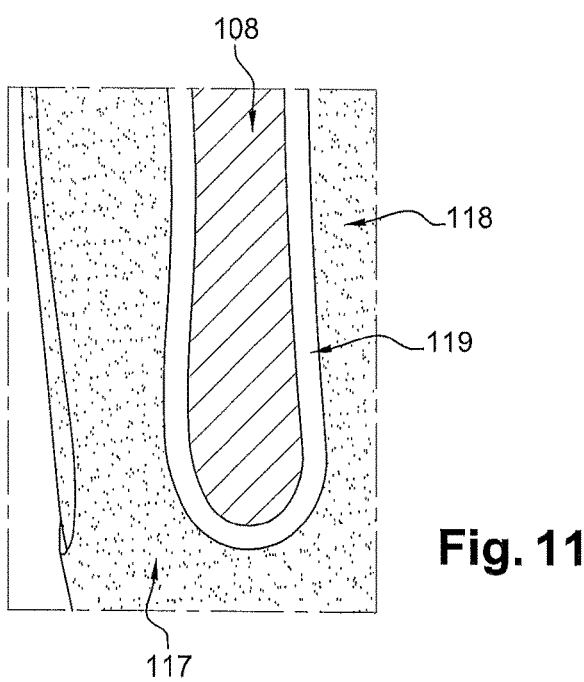
In FIG. 11, a schematic representation of a step for bonding the rigid structure on the positive covered with silicone rubber.

According to a step 720: with reference to FIG. 11, bonding the rigid structure 117 onto the internal layer 108, for example using a silicone adhesive 119 applied on the contact zones between the rigid structure 117 made of carbon and the internal layer 108 made of silicone rubber.

Figure 12:
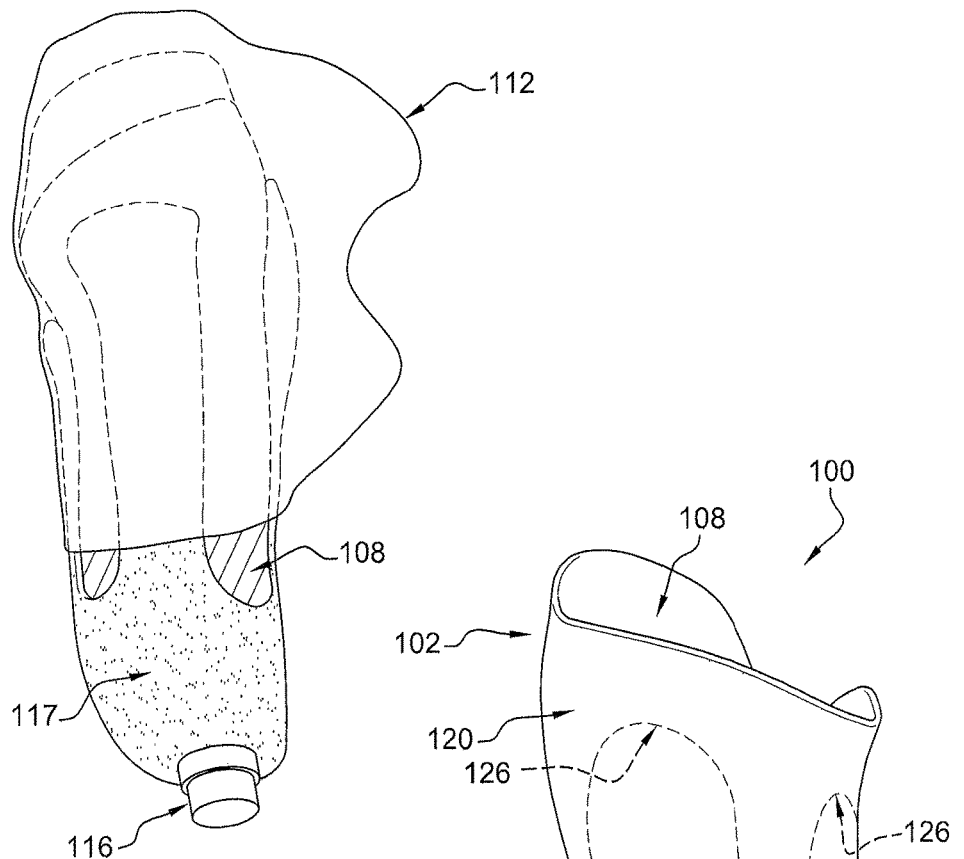
In FIG. 12, a schematic representation of a step for application of silicone rubber on the positive covered with silicone rubber and the rigid structure.

According to a step 721: with reference to FIG. 12, application of a layer of silicone rubber 120 onto the positive 101 covered with the internal layer 108 and the carbon fibre structure 117, so as to cover it with a layer known as the "external layer 120". This step comprises sub-steps similar to those described previously in relation to the application of the internal layer 108.

According to a step 722: creating a vacuum on the positive 101 covered with the internal layer 108, the carbon structure 117 and the external layer 120, in order to ensure good contact between the various layers.

According to a step 723: curing the positive 101 covered with the internal layer 108, the carbon structure 117 and the external layer 120, in order to harden the external layer 120.

According to a step 724: de-moulding the assembly comprising the internal layer 108, the rigid structure 117, and the external layer 120 from the positive 101. In order to do this the plaster positive 101 is broken, for example using a hammer and chisel.

According to a step 725: screwing in the de-pressurisation valve 109, as replacement for the jig 107. It should be noted that gaps have been left beforehand in the carbon fibre 114 around the jig 107, and that neither does the external layer of silicone rubber 120 cover it, so that access to it has been left. The pressurisation valve 109 may thus be placed and screwed into position. FIG. 13 shows the completed socket 100, fixed to a modular element 104. It will be noted that the external layer 120 can contain pigment so as to give it the colour of the patients' skin. Details such as beauty spots, freckles or even hair may also be added.

The socket according to an embodiment of the invention improves the everyday comfort of the patient and offers many benefits:

Its ability to be fitted directly, without the need to use an adaptor, facilitates fitting of the socket. The patient applies cream or another lubricant to the lower limb which has undergone amputation and attached the socket directly. The use of a prosthesis fitting aid is nevertheless still possible. Direct fitting means that the prosthesis can be easily repositioned, because of the flexibility of the socket. This operation therefore becomes quicker. It should be noted that direct fitting is facilitated in the case of lower limbs that have undergone amputation which are long and tonic. The socket is then a contact socket, which can be used without an adaptor, and which provides a comfortable support for the flesh of the lower limb that has undergone amputation because of its internal structure made of silicone rubber.

The full flexibility of the socket in all planes makes the socket comfortable in many situations. When walking, the deformation of the carbon-fibre posts means that support stresses are reduced and a dynamic is created by the energy returned by the socket. The patient's movements are therefore freer and the lower limb which has undergone amputation behaves more naturally under musculo-skeletal stress during walking. The structure made of silicone rubber that fits and forms a single body with the lower limb that has undergone amputation follows the patient's movements, significantly reducing support stresses in the perineal zone. Damping of impacts experienced by the skeleton are observed. In a seated position, the compression of the front and rear posts and the separation of the lateral posts results in improved comfort and a more natural posture. Moreover, this deformation prevents air from entering through the shoulder of the socket around the lower limb that has undergone amputation, prevents consequent loosening, and prevents socket rotation effects around the lower limb that has undergone amputation after an extended period of being seated. Forwards tipping motions of the trunk (for example to pick up an object from the floor) are made significantly easier, by limiting the forces exerted by the socket on the inguinal fold. In effect the silicone rubber curves to match the bending motion. Comfort is also achieved by the reduction in any dorso-lumbar pain as a result of an improved balance of the pelvis, causing a physiologically improved sitting position and a similar trunk/thigh line on both sides. Different types of surfaces are therefore tolerated better by the patient: hard chairs, tilted seating, bicycle seats etc. In general terms, there are increased levels of comfort in various every day and sporting activities. Wearing of the prosthesis can be tolerated more easily for longer periods and there is no need for it to be refitted.

The freedom of muscular action within the socket enhances the tone of the lower limb that has undergone amputation. Since the socket forms a single body with the latter, the patient then has better control over the prosthesis. Increased muscle strength contributes towards improved appearance of the lower limb that has undergone amputation, which is then more stable and allows greater precision of movement during walking. Moreover, the general health of the patient is maintained, which extends their self-sufficiency in the short and long term.

The characteristics of the socket that is manufactured mean that there is good transmission of sensation to the lower limb that has undergone amputation, and improved perception of the walking environment. Proprioperception is therefore improved, which favours control over the prosthesis because of the feeling in the lower limb that has undergone amputation. The patients can thus feel touch through the socket, and through this the nature of the support when sitting. A load (the weight of a child or an item of luggage etc.) can thus be perceived.

There is improved amplitude of joint movements in all planes of movement of the hip because of the flexibility of the socket (abduction and adduction movements in the frontal plane; flexion, extension and rotation movements in the sagittal plane).

The flexibility of the socket allows for changes in the volume of the lower limb that has undergone amputation in the case of muscular tone being regained, in the case of muscular globulisation or gain or loss of weight, or of daily fluctuation due to various factors (oedema, temperature etc.) The socket is therefore less frequently subject to renewal. Moreover, the use of materials with high wear resistance (silicone rubber and carbon fibre) extends the working life of the socket.

The cutting of the socket and the adhesion of the silicone rubber on the skin improve their aesthetic qualities. The socket is more discrete beneath trousers and the buttock shape is retained. It is possible furthermore to customise the silicone rubber by making it almost the same colour as the patient's skin and by adding various details (hair, beauty spots etc.) There is decreased wear on clothing as a result of the removal of stresses due to the socket on the clothing.

The manufactured socket is compatible with all available prosthetic systems (feet, knees) as well as parts for use in water.

The invention claimed is:

1. A socket to interface a lower limb which has undergone amputation and a modular element, to be fastened to the socket at a distal end the socket comprising:
   an internal deformable layer consisting of silicone rubber, designed to be in contact with the lower limb that has undergone amputation;
   an external deformable layer consisting of silicone rubber; and
   a rigid structure arranged between the internal deformable layer and the external deformable layer,
   wherein the socket extends along a longitudinal direction from a proximal end to the distal end, said proximal end defining an outer opening of the socket through which the lower limb that has undergone amputation is received, and
   wherein the rigid structure comprises at least two posts and a base, each post extending along the longitudinal direction of the socket from the base located at the distal portion to an end of the post such that a distance from the end of the post to the proximal end of the socket is less than half a length of the post along said longitudinal direction, wherein ends of the at least two posts are not linked, so that the ends separate and approach each other due to an effect of a deformation of the internal layer and of the external layer, wherein the at least two posts and the base of the rigid structure are made together from a single monolithic rigid material, and
   wherein, between two successive posts of the at least two posts, a first part of the external deformable layer is in contact with a first part of the internal deformable layer and wherein each of the at least two successive posts separates a second part of the external deformable layer from a second part of the internal deformable layer.

2. The socket according to claim 1, wherein the rigid material comprises carbon.

3. The socket according to claim 1, wherein the rigid structure comprises four posts.

4. The socket according to claim 1, further comprising, at the distal end, a fastener secured to the rigid structure, the fastener configured to directly attach the modular element firmly to the rigid structure made of the rigid material.

5. The socket according to claim 4, wherein the modular element is a knee, a tube or a foot.

6. The socket according to claim 1, further comprising a silicon adhesive provided on contact zones between the rigid structure and the internal deformable layer.

7. The socket according to claim 1, wherein the internal deformable layer and the external deformable layer are distinct layers with different characteristics.

8. The socket according to claim 7, wherein the external deformable layer contains coloring pigments.

\* \* \* \* \*